(12) United States Patent
Diaz et al.

(10) Patent No.: US 7,628,784 B2
(45) Date of Patent: Dec. 8, 2009

(54) BALLOON CATHETER WITH IMPROVED RESISTANCE TO NON-DEFLATION

(75) Inventors: Joseph Robert Diaz, Covington, GA (US); Ian Capstick, Goose Creek, SC (US)

(73) Assignee: C. R. Bard, Inc., Murray Hill, NJ (US)

( * ) Notice: Subject to any disclaimer, the term of this patent is extended or adjusted under 35 U.S.C. 154(b) by 548 days.

(21) Appl. No.: 10/338,768

(22) Filed: Jan. 6, 2003

(65) Prior Publication Data

US 2004/0133156 A1 Jul. 8, 2004

(51) Int. Cl.
*A61M 27/00* (2006.01)
(52) U.S. Cl. ..................................... 604/544
(58) Field of Classification Search ............ 604/101.03, 604/102.02, 103.05, 103.06, 103.09, 526, 604/96.01, 194, 913, 523
See application file for complete search history.

(56) References Cited

U.S. PATENT DOCUMENTS

| 2,819,718 | A | * | 1/1958 | Goldman | 604/103.09 |
|---|---|---|---|---|---|
| 3,926,705 | A | | 12/1975 | Todd | |
| 3,983,879 | A | * | 10/1976 | Todd | 604/96.01 |
| 4,284,081 | A | * | 8/1981 | Kasper et al. | 604/102.02 |
| 4,335,723 | A | * | 6/1982 | Patel | 604/97.02 |
| 4,447,228 | A | | 5/1984 | Patel | |
| 4,464,176 | A | | 8/1984 | Wijayarathna | |
| 4,861,337 | A | * | 8/1989 | George | 604/103.09 |
| 5,320,908 | A | | 6/1994 | Sodervall et al. | |
| 5,342,303 | A | * | 8/1994 | Ghaerzadeh | 604/102.01 |
| 5,370,615 | A | * | 12/1994 | Johnson | 604/102.02 |
| 5,395,651 | A | | 3/1995 | Sodervall et al. | |
| 5,747,178 | A | | 5/1998 | Sodervall et al. | |
| 5,964,971 | A | * | 10/1999 | Lunn | 156/86 |
| 5,965,204 | A | | 10/1999 | Sodervall et al. | |
| 6,030,369 | A | * | 2/2000 | Engelson et al. | 604/264 |
| 6,368,302 | B1 | * | 4/2002 | Fitzmaurice et al. | 604/103.04 |
| 2001/0021840 | A1 | * | 9/2001 | Suresh et al. | 604/525 |
| 2002/0061375 | A1 | * | 5/2002 | Cartledge et al. | 428/36.9 |

FOREIGN PATENT DOCUMENTS

WO    WO 99/37349    7/1999

* cited by examiner

*Primary Examiner*—Nicholas D Lucchesi
*Assistant Examiner*—Christopher D Koharski
(74) *Attorney, Agent, or Firm*—Rutan & Tucker, LLP

(57) ABSTRACT

Balloon catheters are disclosed that comprise a material that confers improved resistance to non-deflation. Balloon catheters are also disclosed that comprise a reduced drainage lumen diameter. In some embodiments the catheters achieve these characteristics without rendering the catheters undesirably stiff.

41 Claims, 4 Drawing Sheets

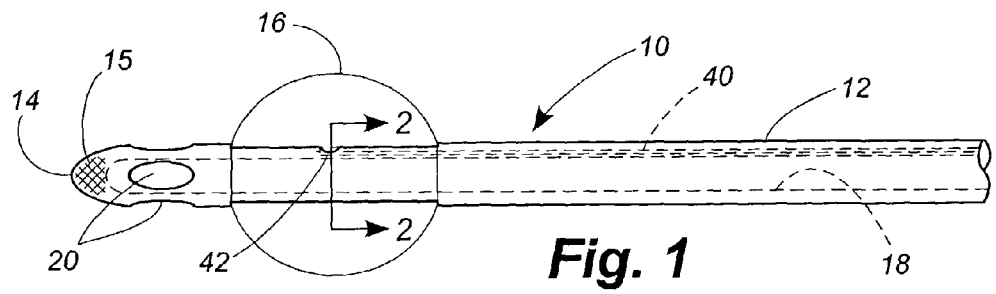
Fig. 1
PRIOR ART
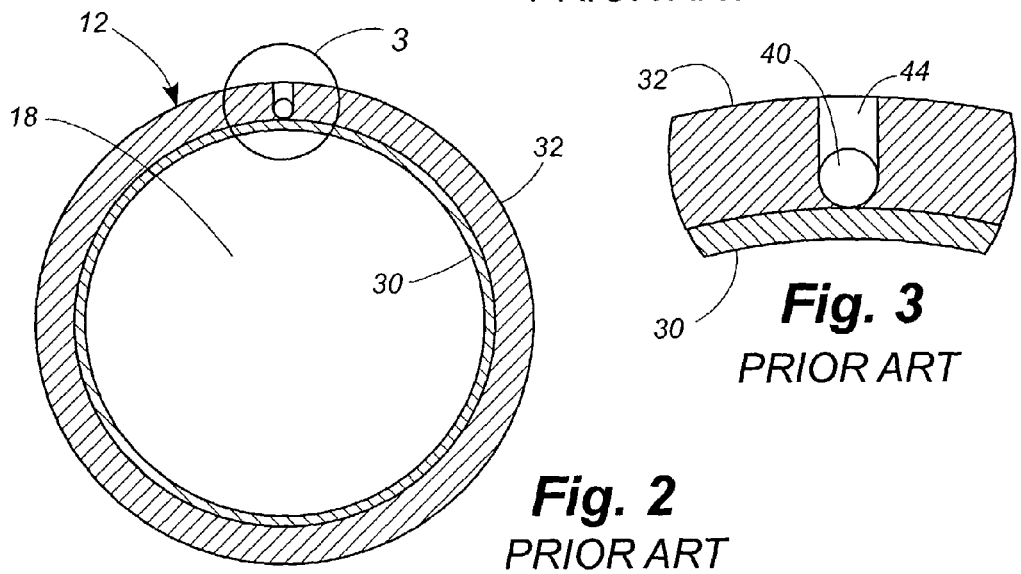
Fig. 2
PRIOR ART
Fig. 3
PRIOR ART
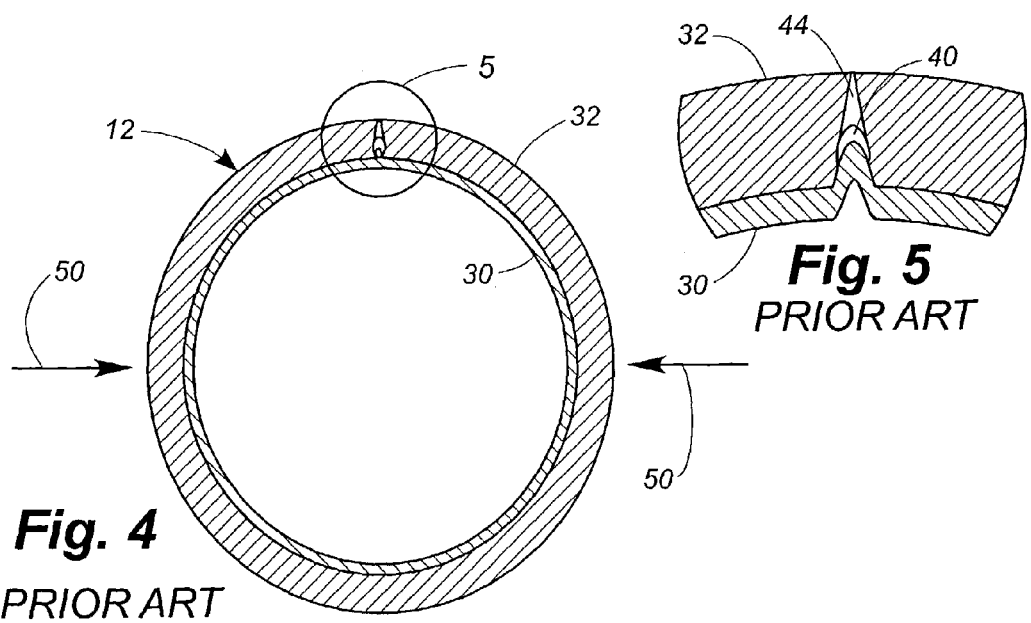
Fig. 4
PRIOR ART
Fig. 5
PRIOR ART

BALLOON CATHETER WITH IMPROVED RESISTANCE TO NON-DEFLATION

TECHNICAL FIELD

The present invention relates generally to balloon catheters and relates more specifically to a balloon catheter that exhibits improved resistance to non-deflation.

BACKGROUND OF THE INVENTION

Balloon catheters are well known medical devices in which an inflatable member is located adjacent to the distal end of the catheter shaft and inflated once the catheter is positioned within the body of the patient to anchor the distal end. Such catheters comprise an elongated shaft defining a drainage lumen and an inflation lumen. The drainage lumen comprises a major portion of the cross-section of the catheter shaft and is closed at its distal end by a tip portion. Openings or ports distal to the balloon permit fluid to enter the drainage lumen. The proximal end of the drainage lumen is placed in fluid communication with a method of drainage such as a urinary drainage bag. In some embodiments, the communication is made through a drainage funnel located at the proximal end of the catheter through which the drainage lumen opens.

The inflation lumen is formed within the wall of the catheter shaft and extends from a location inside of the balloon, along the catheter shaft, and through an opening, typically a branch adjacent the proximal end of the shaft. An inflation valve at the end of the branch or other opening permits fluid to be infused into the inflation lumen.

For urinary catheters such as Foley catheters, the catheter is introduced into the patient and is advanced into the urethra and advanced until the distal end of the catheter, including the balloon, resides within the bladder. The balloon is then inflated, typically by coupling a syringe to the inflation valve and actuating it to discharge fluid from the syringe, through the inflation lumen, and into the balloon.

To remove a balloon catheter, it is first necessary to deflate the balloon anchoring the distal end of the catheter. This is done by withdrawing fluid through the inflation lumen, typically through a syringe coupled to inflation lumen through an inflation valve. On occasion, it proves difficult or impossible to deflate the balloon in the normal manner. When this happens, it becomes necessary to take extraordinary means such as inserting an instrument up the catheter through the inflation lumen or through the bladder to pierce the balloon to allow the inflation medium to escape. Addition of mineral oil can also be used to cause the balloon to weaken and rupture. These procedures may cause the patient additional discomfort and may lead to adverse clinical consequences.

Thus there is a need for a balloon catheter with improved resistance to non-deflation.

SUMMARY OF THE INVENTION

Stated generally, the present invention comprises a balloon catheter with enhanced resistance to non-deflation. The invention is based on the discovery that most non-deflating balloons are the consequence of the inflation lumen collapsing under radial pressure exerted against the balloon and hence against the underlying catheter shaft. In addition, the negative pressure exerted within the inflation lumen by the syringe trying to withdraw fluid from the balloon will further collapse the walls of the lumen, making fluid withdrawal difficult or impossible. This invention is further based on the discovery that by increasing the stiffness of the material making up the innermost portion of the wall of the catheter shaft, the patency of the inflation lumen can be maintained, making it possible to deflate the balloon under a wider range of circumstances. Surprisingly, these results occur even though the stiffened material is located interior to the inflation lumen (i.e. closer to the center of the catheter diameter than the inflation lumen) rather than surrounding or exterior to the inflation lumen. It has further been found that increasing the stiffness of only the innermost material achieves these desirable results without the undesirable consequences of significantly increasing the stiffness of the catheter.

Objects, features, and advantages of the present invention will become apparent upon reading the following specification, when taken in conjunction with the drawings and the appended claims.

BRIEF DESCRIPTION OF THE DRAWINGS

FIG. 1 is a side view of a PRIOR ART balloon catheter.

FIG. 2 is a cross-sectional view of the PRIOR ART balloon catheter of FIG. 1 taken along line 2-2 of FIG. 1.

FIG. 3 is an enlarged view of the area of the cross-section of FIG. 2 designated by the circle 3.

FIG. 4 is another cross sectional view of the PRIOR ART balloon catheter of FIG. 1, taken along line 2-2 of FIG. 1, with the balloon under abnormally high radially inward pressure.

FIG. 5 is an enlarged view of the area of the cross-section of FIG. 4 designated by the circle 5.

DETAILED DESCRIPTION OF THE DISCLOSED EMBODIMENT

Figure 6:
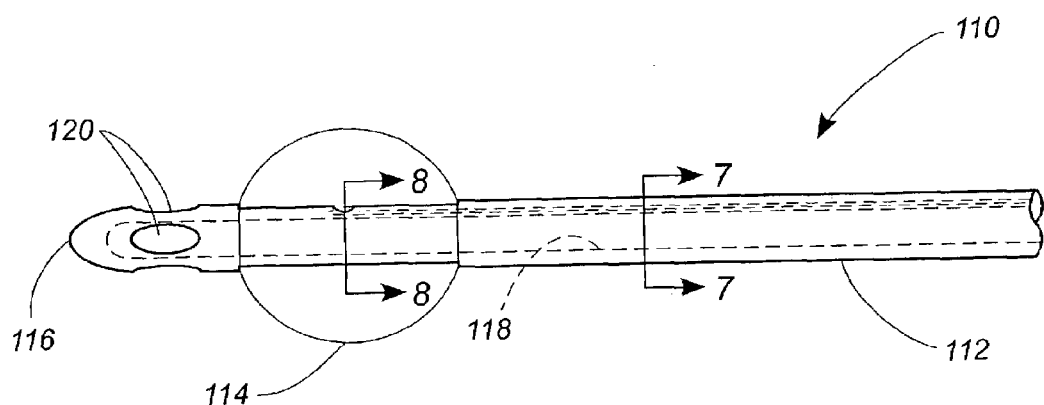
FIG. 6 is a side view of a balloon catheter according to a disclosed embodiment of the present invention.

Reference is now made to the drawings, in which like numerals indicate like elements throughout the several views. FIGS. 1-5 illustrate a PRIOR ART balloon catheter 10. The balloon catheter 10 includes a shaft 12, a tip 14, a fabric reinforcing cap 15, and a balloon 16. A drainage lumen 18 is formed within the shaft and communicates with the ambient surrounding the tip 14 by way of radial drainage eyes 20.

Viewed in cross-section as in FIGS. 2-5, the catheter shaft 12 beneath the balloon 16 comprises two layers, an inner or "rubberize" layer 30 and an intermediate or "build up" layer 32. Conventionally, the rubberize layer 30 and the build up layer 32 are formed from the same or similar material, typically latex or silicone, such that the resulting composite structure is essentially homogenous.

It will be appreciated that, when viewed in cross section at locations along the shaft that do not lie beneath the balloon, the shaft in some embodiments actually comprises three layers, the inner or rubberize layer 30, the intermediate or build up layer 32, and an outer or "finish" layer bonded to the outer surface of the intermediate or build up layer. The references to materials herein as being "bonded" to one another refers to such materials being attached to each other by any means, including but not limited to bonds, attractions, or crosslinks formed between the materials themselves as well as binders or adhesives used to form bonds, attractions, or crosslinks to each material. However, the outer or finish layer is not bonded to the intermediate or build up layer 32 at the axial locations corresponding to the balloon and is thus capable of expanding away from the build up layer 32.

Formed within the build up layer 32 is a longitudinal inflation lumen 40. Although the figures show an embodiment in which the inflation lumen 40 has its lower edge touching the rubberize layer 30, embodiments also exist in which the inflation lumen is surrounded completely by the build up layer 32. The inflation lumen 40 runs parallel to the surface of the build up layer 32 until a point 42 beneath the balloon 16, where it turns radially outward and communicates with the interior of the balloon. The portion that extends in a radial direction and communicates with the interior of the balloon 16 is known as the "inflation eye" 44. At the opposite end of the inflation lumen 40, the lumen branches off from the catheter shaft 12 and terminates at an inflation valve (not shown). A syringe engages the inflation valve in the conventional manner to infuse an inflation medium such as sterile water through the inflation lumen 40 to inflate the balloon 16.

FIG. 3 is an enlarged view of the portion identified by the circle 3 in FIG. 2. In FIG. 3 the inflation lumen 40 and inflation eye 44 can be seen. Because the balloon (not visible in FIGS. 2 and 3) surrounding the inflation eye 44 is not under significant radial inward pressure, the inflation eye 44 and inflation lumen 40 in FIGS. 2 and 3 are patent.

Referring now to FIGS. 4 and 5, the balloon (again, not seen in FIGS. 4 and 5) is under abnormally high radially inward pressure. This radially inward pressure can result from any number of causes, including but not limited to under-inflation of the balloon, anatomical abnormality, excessive traction resulting from physician placement or patient movement, etc. The radially inward pressure exerted on the balloon results in a radially inward pressure exerted on the catheter shaft 12, as indicated by the arrows 50. This pressure compresses the shaft horizontally and causes it to elongate vertically. As can be seen in FIG. 5, this vertical elongation causes the rubberize layer 30 to distort into the inflation lumen 40, closing or very nearly closing off the inflation lumen 40. In addition, when a negative pressure is exerted by a syringe trying to aspirate fluid from the balloon 16, the effect can be to completely collapse the walls of the inflation lumen 40, making it difficult or impossible to deflate the balloon.

A balloon catheter 110 of the present invention addresses these problems and exhibits enhanced resistance to non-deflation. Referring now to FIG. 6, the catheter 110 comprises an elongated catheter shaft 112. A balloon 114 is located adjacent the forward tip 116 of the catheter shaft 112. A drainage lumen 118 extends longitudinally within the catheter shaft 112 and terminates just short of the tip 116. The drainage lumen 118 is in communication with the ambient surrounding the tip 116 by way of a plurality of radial drainage eyes 120.

Figure 7:
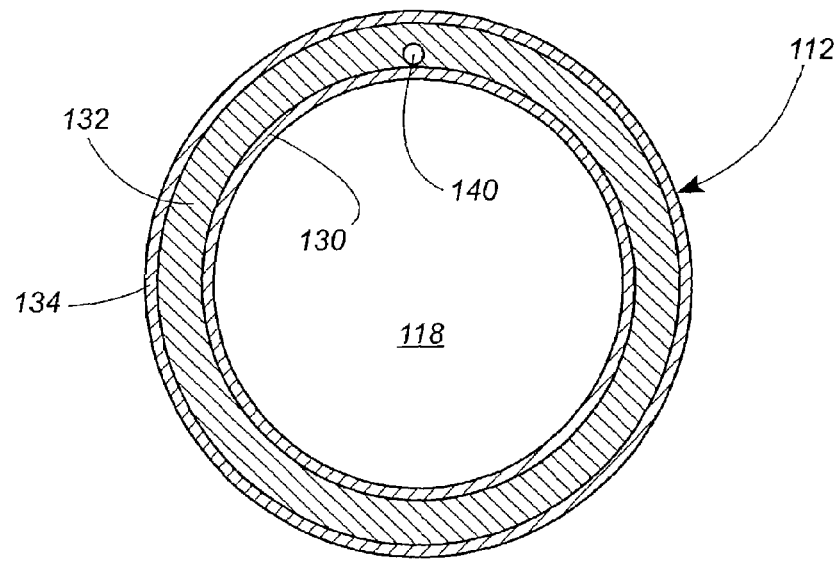
FIG. 7 is a cross-sectional view taken along line 7-7 of FIG. 6.

FIG. 7 is a cross-sectional view of the catheter shaft 112 as seen along line 7-7 of FIG. 6. The shaft is formed from three distinct layers: an innermost or rubberize layer 130, an intermediate or build up layer 132, and an outermost or finish layer 134. It will be appreciated, however, that the presence of the finish layer is not critical to the invention and that embodiments exist in which the catheter lacks a finish layer. Formed within the build up layer 132 and having its lower edge in contact with the rubberize layer 130 is an inflation lumen 140.

Figure 8:
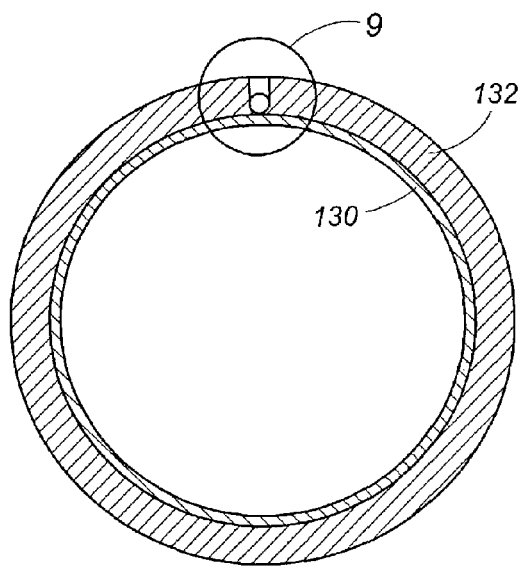
FIG. 8 is a cross-sectional view taken along line 8-8 of FIG. 6.
Figure 9:
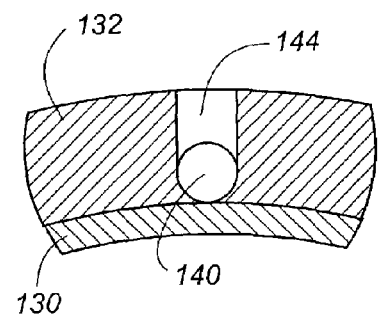
FIG. 9 is an enlarged view of the portion of the cross-sectional view of FIG. 8 designated by the circle 9.

FIG. 8 is a cross-sectional view of the catheter shaft 112 as seen along line 8-8 of FIG. 6. Not seen in FIG. 8, the finish layer 134 is expanded away from the build up layer 132 as the balloon 116 is inflated, leaving only the rubberize layer 130 and build up layer 132 visible. FIG. 9 is an enlargement of the portion of FIG. 8 designated by the circle 9 and shows the inflation lumen 140 and a radial inflation eye 144 that places the inflation lumen in communication with the space between the build up layer 132 and the balloon 116.

Figure 10:
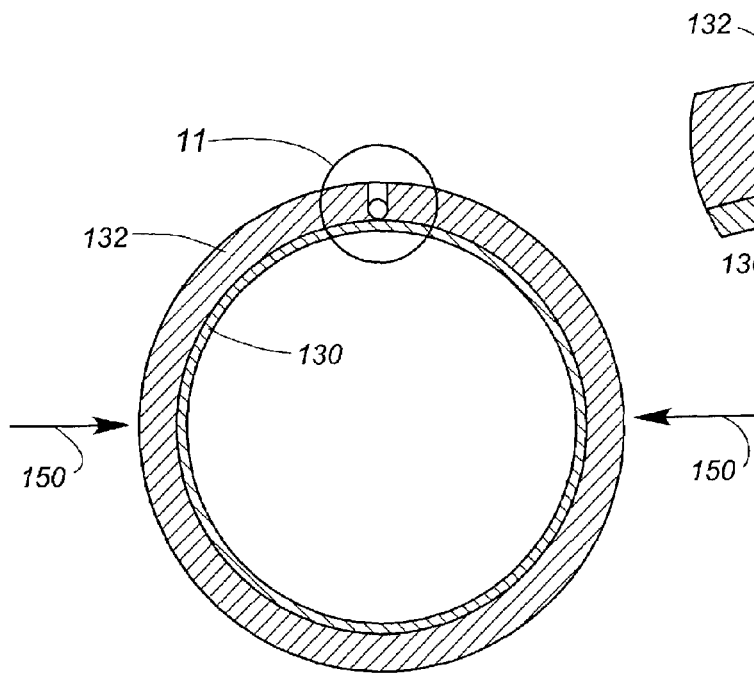
FIG. 10 is a cross-sectional view of the balloon catheter of FIG. 6, taken along line 8-8 of FIG. 6, with the balloon under abnormally high radially inward pressure.
Figure 11:
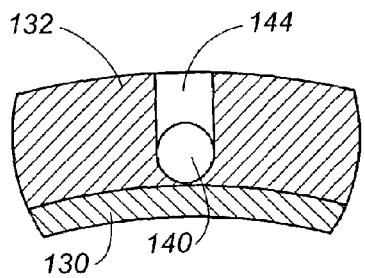
FIG. 11 is an enlarged view of the portion of the cross-section of FIG. 10 designated by the circle 11.

FIG. 10 is another cross-sectional view similar to FIG. 8, but in FIG. 10 the balloon is subject to abnormally high radially inward pressures. As previously explained with respect to FIG. 4, such abnormally high radially inward pressure can result from any number of sources, including under-inflation of the balloon, anatomical abnormality, the physician pulling too hard on the catheter to seat the balloon in the neck of the bladder, etc. The radially inward pressure exerted on the balloon results in a radially inward pressure exerted on the catheter shaft 112, as indicated by the arrows 150. This pressure compresses the shaft horizontally and causes it to elongate vertically. However, unlike the inflation lumen 40 and inflation eye 44 seen in the catheter 10 of FIG. 5, the vertical elongation of the catheter 110 does not cause the inflation lumen 140 and the inflation eye 144 to distort. The inflation lumen 140 and inflation eye 144 of the catheter 110 of FIGS. 10 and 11 remain patent, permitting the balloon 114 to deflate normally. The reasons for the increased resistance to non-deflation will now be explained.

The relative stiffnesses of the various layers 130, 132, and 134 of the balloon catheter 110, as expressed by their Young's moduli, are controlled. The catheters of the present invention include an inner rubberize layer 130 of material having a Young's Modulus that is higher than the Young's Modulus of the middle layer 132. In some embodiments having both a middle layer 132 and an outer layer 134, the Young's Modulus of the inner layer is higher than that of both the middle layer 132 and the outer layer 134. As used herein, Young's Modulus refers to the Modulus of Elasticity when determined according to standard procedures such as American Society for Testing and Materials (ASTM) Method E-111-82 using sample preparation procedures set forth in ASTM Method D-412-98a. As used herein, "wet" Young's Modulus shall refer to Young's Modulus measured after immersion of a material in deionized water at a temperature of 60-85° F. for a period of 4-5 days. As used herein, "dry" Young's Modulus shall refer to Young's Modulus of a material that has not been immersed.

The wet Young's Modulus of the material used to form the inner or rubberize layer 130 is significantly higher than the wet Young's Modulus of the material used to form the build up layer 132. In some embodiments, the material used to form the inner or rubberize layer 130 has a wet Young's Modulus of at least about 1.5 times the wet Young's Modulus of the material used to form the build up layer 132. In some embodiments, the material used to form the inner or rubberize layer 130 has a wet Young's Modulus of at least about 2 times the wet Young's Modulus of the material used to form the build up layer 132. In some embodiments, the material used to form the inner or rubberize layer 130 has a wet Young's Modulus of at least about 3 times the wet Young's Modulus of the material used to form the build up layer 132. In some embodiments, the material used to form the inner or rubberize layer 130 has a wet Young's Modulus of from about 70 psi to about 120 psi and the material used to form the build up layer 132 has a wet Young's Modulus of from about 20 pounds per square inch (psi) to about 40 psi. In some embodiments, the material used to form the inner or rubberize layer 130 has a wet Young's Modulus of about 85 psi, and the material used to form the build up layer 132 has a wet Young's Modulus of about 27 psi. Each of the foregoing embodiments are practiced using any material or combinations of materials to form the three layers. Variations on each of the above embodiments exist in which the catheter possesses a finish layer 134. In some of these variations, the Young's Modulus of the finish layer 134 is essentially the same as that of the build up 132 layer, meaning that for such variations on the embodiments the above comparisons of rubberize layer 130 to build up layer 132 is a comparison of the rubberize layer 130 to both the build up 132 and finish 134 layers.

In some embodiments, the material used to form the inner rubberize layer 130 has a wet Young's Modulus of at least about 50 psi, while the Young's Modulus of the material used to form the build up layer 132 is significantly below 50 psi. In some embodiments, the material used to form the inner rubberize layer 130 has a wet Young's Modulus of at least about 80 psi while the wet Young's Modulus of the material used to form the build up layer 132 is significantly below 50 psi. Embodiments also exist in which the material used to form the rubberize layer 130 has a wet Young's Modulus of at least about 100 psi. Embodiments also exist in which the rubberize layer 130 has a wet Young's Modulus of at least about 200 psi. In some embodiments, the material used to form the inner rubberize layer 130 has a wet Young's Modulus of at least about 250 psi. In one embodiment, the material used to form the inner rubberize layer 130 has a wet Young's Modulus of between about 80 psi and about 90 psi while the Young's Modulus of the build up layer 132 is between about 25 psi and about 30 psi. Variations on each of the above embodiments exist in which the catheter possesses a finish layer 134. In some of these variations, the Young's Modulus of the finish layer 134 is essentially the same as that of the build up 132 layer, meaning that for such variations on the embodiments the above comparisons of rubberize layer 130 to build up layer 132 is a comparison of the rubberize layer 130 to both the build up 132 and finish 134 layers.

In some embodiments, the Young's Modulus of the material used to form the rubberize layer 130 shows less propensity to decrease upon immersion than those of prior art rubberize materials. In some embodiments, the material used to form the rubberize layer 130 has a wet Young's Modulus that is at least about 50% of its dry Young's Modulus. In other embodiments, the material used to form the rubberize layer material has a wet Young's Modulus that is at least about 60% of its dry Young's Modulus. In other embodiments the material used to form the rubberize layer 130 has a wet Young's Modulus that is at least about 70% of its dry Young's Modulus. In other embodiments, the material used to form the rubberize layer 130 has a wet Young's Modulus that is about 70% of its dry Young's Modulus.

In some embodiments, Young's Moduli of the different layers in the catheter are varied by forming the layers from materials having different Young's Moduli. Any method can be used to prepare catheters having layers made of different materials. Examples of such methods include, but are not limited to, successive dipping of a form in different materials, extrusion or coextrusion of different layers, and molding of the different layers. Any combination of methods may also be used. For example, in one embodiment an extruded, coextruded, or molded material is subsequently dipped in a different material to add another layer.

Materials commonly used to make catheters 110 include, but are not limited to natural rubber latexes (available, for example, from Guthrie, Inc., Tucson, Ariz.; Firestone, Inc., Akron, Ohio; and Centrotrade USA, Virginia Beach, Va.), silicones (available, for example, from GE Silicones, Waterford, N.Y., Wacker Silicones, Adrian, Mich.; and Dow Corning, Inc., Midland, Mich.), polyvinyl chlorides (available, for example, from Kaneka Corp., Inc., New York, N.Y.), polyurethanes (available, for example, from Bayer, Inc., Toronto, Ontario, Rohm & Haas Company, Philadelphia, Pa.; and Ortec, Inc., Greenville, S.C.), plastisols (available, for example, from G S Industries, Bassett, Va.), polyvinyl acetate, (available, for example from Acetex Corp., Vancouver, British Columbia) and methacrylate copolymers (available, for example, from Heveatex, Inc., Fall River, Mass.). Natural rubber latexes, polyurethanes, and silicones are preferred materials. Any combination of the foregoing materials may also be used in making catheters. In one embodiment, a rubberize layer that includes latex and a methacrylate is used with build up and finish layers that include latex but not methacrylate. In another embodiment, a polyurethane rubberize layer is used with latex build up and finish layers. In another embodiment, a polyvinyl acetate and latex rubberize layer is used with latex build up and finish layers. Each of the foregoing embodiments in which specific Young's Modulus values are specified may be used with any material.

The above list of materials that can be used above in making catheters is not intended to be exhaustive and any other materials that can be used are within the scope of the invention. In addition, catheters of the present invention are not limited to those having three layers of material. For example, one or more additional coatings may applied to the surface of the catheters to provide lubricity, to reduce risk of infection, or for any other purpose. Any combination of layers can be used.

The Young's Modulus of materials used in making catheters can be manipulated through a variety of methods. Any method for manipulating the Young's Modulus may be used. For natural rubber latex for example, additives can be incorporated to increase the Young's Modulus. Examples include, but are not limited to: methacrylate grafted copolymer, vinyl chloride, acrylonitrile, styrene, polyvinyl acetate, high-styrene butadiene, clay, calcium carbonate, barium sulfate, zinc oxide, soluble silicate, or combinations of the foregoing. The Young's Modulus can also be controlled by adjusting the level of the foregoing additives in the composition. For silicones, the Young's Modulus can be controlled by changing the molecular weight of the material or altering the degree of cross-linking or mixing silicones of different molecular weights and crosslinking. For polyvinyl chlorides and plastisols, the Young's Modulus can be manipulated by changing the molecular weight of the material or varying the amount of plasticizer added. Examples of plasticizers include dioctyl phthalate, nitrocellulose, and diisodectylglutarate. For polyurethanes, the Young's Modulus can be manipulated by changing the molecular weight of the polymer, changing orientation of monomers, and modifying the degree of cross-linking. In some embodiments, one or more methacrylates are copolymerized with one or more latexes, and the relative amounts of the methacrylates and latexes in the polymer are manipulated to control the Young's Modulus. In some embodiments, one or more PVAs are present in a mixture with one or more latexes, and the relative amounts of the PVAs and latexes in the mixture are manipulated to control the Young's Modulus.

The balloon catheter 110 of the disclosed embodiment is manufactured by dipping. An elongated rod or "form" is dipped into a first liquid coating material to form a layer of coating material on the form. The form has the shape and dimensions of the drainage lumen 118 of the catheter. This first coating layer forms the inner or rubberize layer 130 of the catheter. Once the first layer 130 has dried, an elongated wire is attached longitudinally to the outside of the first layer. The form with first layer 130 and wire is then dipped into a second coating material to build up an intermediate or build up layer 132. Multiple dips into the second coating material are necessary to build up an intermediate layer 132 of appropriate thickness. The inflation eye 144 is then formed near the distal end of the second layer 132 to place the inflation lumen 140 in communication with the ambient surrounding the second layer 132. The build up layer 132 is then dried. The finish layer 134 is applied with a subsequent dip and is dried.

The balloon can be formed in a number of ways, and any method for forming the balloon may be used. In some preferred embodiments, the balloon is formed by the application of a pre-formed balloon component on the second layer 132. In one of these embodiments, a finish layer 134 is used and is applied over the pre-formed balloon component and thus forms part of the wall of the balloon. In another of these embodiments, no finish layer 134 is used and the pre-formed balloon component forms the entire wall of the balloon. In other embodiments, a masking material is applied to the exterior of the second layer 132 in the balloon formation area such that a bond does not form between the build up layer 132 and the finish layer 134 in the area surrounding the inflation eye 144 of the inflation lumen 140. In such latter embodiments, the unadhered portion of the finish layer 134 becomes the inflatable balloon 116. Regardless of the method used to form the balloon, the form with first and second layers 130, 132 and the balloon formation is then dipped into a third coating solution to build up the outer or finish layer 134. Once the outer layer 134 has been dried, the catheter 110 is removed from the form. The space formerly occupied by the form and the inflation wire become the drainage and inflation lumens 118 and 140 (respectively). Drainage eyes 120 are then formed in the catheter shaft 112 adjacent its distal end 116 to place the drainage lumen 118 in communication with the ambient surrounding the forward end of the shaft 112.

The balloon is inflated by infusing an inflation medium out of the inflation eye 144 of the inflation lumen 140 and into the balloon.

To introduce an uninflated balloon catheter 110 into a patient, a stylet may be inserted into the proximal end opening of the drainage lumen (for example, the opening of a drainage funnel) of the catheter and advanced until the forward end of the stylet bears against the inside of the forward tip 116 of the catheter. The catheter 110 with the stylet affixed is then advanced through the urethra and into the neck of the bladder. Because all of the force drawing the catheter 110 along into place is being exerted against a single point in the tip 116 of the catheter 110, it has heretofore typically been necessary to embed a fabric reinforcement cap within the wall of the catheter tip to spread out the forces exerted by the stylet over a greater area of the catheter tip 116. An unexpected advantage of stiffening the innermost layer 130 of the catheter 110 is that the innermost layer is now able to withstand the forces exerted upon it by the stylet tip without the need for reinforcement, thereby eliminating the need for the embedded fabric and thus substantially simplifying construction.

In some embodiments, resistance to non-deflation is improved by increasing the thickness of the rubberize layer 130 and correspondingly reducing the diameter of the drainage lumen 118; that is, by reducing the inner diameter, the rubberize layer can be increased while maintaining the same overall outside dimensions, along with the dimensions of all other layers. It has been found that reducing the diameter of the drainage lumen increases the resistance to lumen collapse. In some embodiments, drainage lumen diameter is reduced by 15% as compared to prior art catheters. In some embodiments, the drainage lumen diameter is less than about 50% of the outer diameter of the catheter. In other embodiments, the drainage lumen diameter is between about 40% and about 50% of the outer diameter of the catheter. In other embodiments, the drainage lumen diameter is between about 45% and 50% of the outer diameter of the catheter. In other embodiments, the drainage lumen diameter is between about 40% and 45% of the outer diameter of the catheter. In some embodiments, the drainage lumen diameter is less than about 40% of the outer diameter of the catheter. In one embodiment, the drainage lumen diameter is about 46% of the outer diameter of the catheter. For example, in one embodiment, the drainage lumen of a 16 French catheter (having an outer diameter of about 0.208 inches) has a diameter less than 0.100 inches, preferably 0.093 inches. Reducing the drainage lumen diameter is accomplished by any means including, but not limited to, using a form having a smaller diameter. Reducing the drainage lumen diameter as it relates to the outer diameter is accomplished by any means including, but not limited to, using a form having a smaller diameter while increasing the thickness of one or more of the layers of the catheter. In a preferred embodiment, the drainage lumen diameter is decreased by reducing the diameter of the form while the outer diameter of the catheter is retained by thickening the rubberize layer. In some embodiments, reducing the drainage lumen diameter is used in conjunction with increasing the Young's Modulus of the rubberize layer to improve resistance to non-deflation. In other embodiments, reducing the drainage lumen diameter alone is used to improve resistance to non-deflation. In still other embodiments, increasing the Young's Modulus of the rubberize layer alone is used to improve resistance to non-deflation.

"Tip Penetration Test" to Measure Resistance to Tip Penetration

For purposes of this application, "tip penetration" values are values measured using the tip penetration test described below. The test determines resistance to tip penetration. All tip penetration values presented in this application are generated based on this test. Specific test parameters used for the test results described herein are set forth in parentheses.

Each catheter is cut to yield a shaft sample approximately 2 inches long, including a catheter tip. Tip penetration force is determined using an INSTRON #4300 Tensile-System to apply and to measure tensile force, although any equivalent means of applying and measuring tensile force may be used. The INSTRON device has two jaws that can be pulled apart or compressed together at specified speeds in a direction that is essentially perpendicular to the horizontal while measuring the tension or compression forces, (measured in pounds). A Catheter Tip Pull Test Fixture of the type described in European Standard EN-1616:1997 is attached to the top jaw of the Tensile Testing device. The Catheter Tip Pull Test Fixture has a supporting member that includes a steel pin as a fixed member. The sample is placed onto the Tip Pull Test Fixture by inserting the pin into one of the drainage eyes of the catheter in such a direction that the interior wall of the catheter tip is in contact with the pin. The pin serves to simulate the tip of a stylet used to insert a catheter. Specifically, the pin has a diameter of approximately 70-80% of that of the drainage lumen of the catheter (for the data reported herein the pin had a diameter 0.078 inches and the catheters tested had lumen diameters of approximately 0.100 inches) and is round in cross-section with a radiused tip. The supporting member and pin are disposed in the top jaw of the INSTRON or equivalent device such that the axis of the pin runs in a direction that is essentially perpendicular to the horizontal. The pin is of sufficient length (the data disclosed herein involved use of a pin having a length of 0.772 inches) such that the entire weight of the catheter is supported by the pin during the test. The other end of the sample is fixed by the bottom jaw of the Tensile Testing device. Separation between the bottom jaw of the INSTRON or equivalent device and Catheter Tip Pull Test fixture was approximately 3-4 inches. The Tensile Testing device is then set to pull the jaws apart in a vertical direction at a rate of 20 inches per minute until the tip was penetrated, and the force applied to the catheter is measured by the Tensile Testing device. The force at which tip penetration occurred is recorded.

"Hand" Test to Measure Catheter Stiffness.

Figure 12:
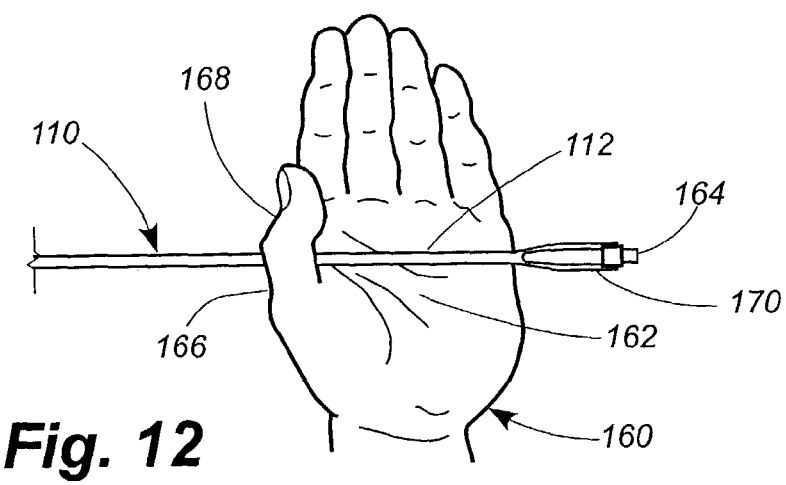
FIG. 12 is a top view of the palm of the hand of a tester holding a catheter in a first step of a Hand test for catheter stiffness.
Figure 13:
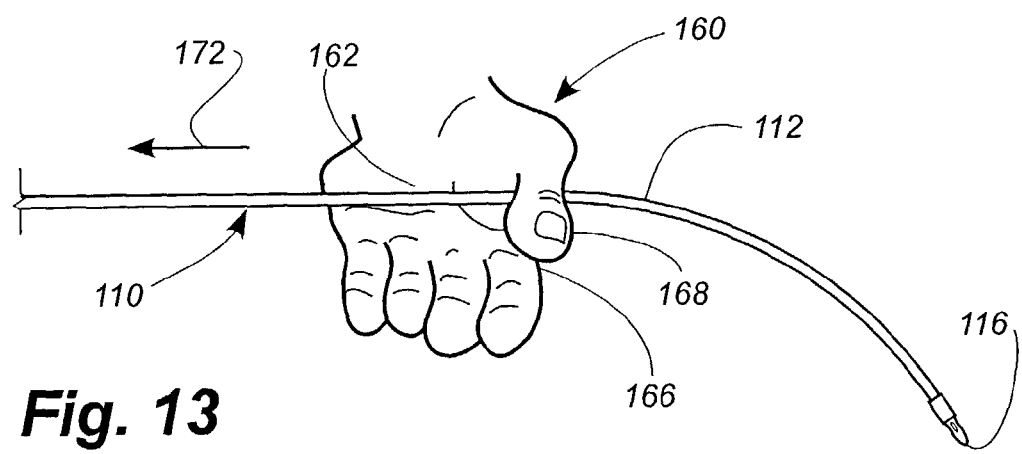
FIG. 13 is a front view of the hand of the tester of FIG. 12 holding the catheter in a second step of the Hand test for catheter stiffness.
Figure 14:
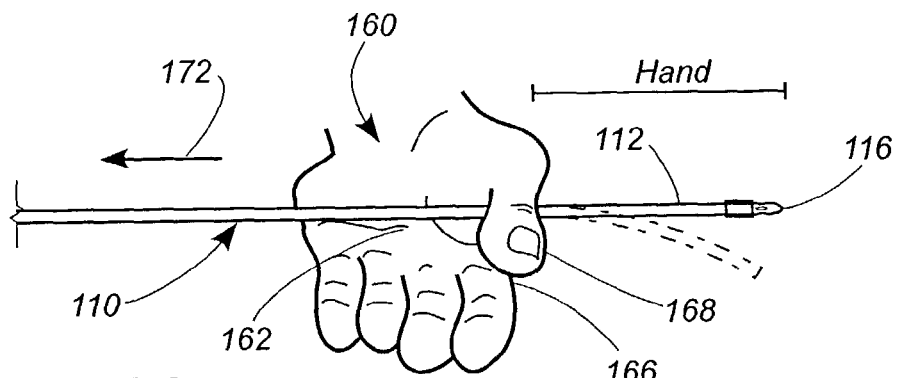
FIG. 14 is a front view of the hand of the tester of FIG. 12 holding the catheter in a third step of the Hand test for catheter stiffness.

For purposes of this application, "hand" values refer to values determined through the Hand Test procedures set forth below. The Hand Test is a relative measure of the catheter stiffness. The following procedures were used to perform the Hand Test. Referring to FIGS. 12-14, a hand 160 of a tester was held outward, palm 162 facing upward and held generally horizontal. The shaft 112 of a catheter 110 near the inflation port 164 was placed in the palm 162, with the major portion of the catheter shaft hanging off of the thumb side 166 of the hand 160. The inflation lumen was oriented upward, and the thumb 168 of the hand 160 was placed on top of the catheter shaft 112 to maintain that orientation. The other hand grasped the funnel 170 of the catheter 110 and gently pulled the catheter between the thumb 168 and palm 162 of the first hand 160 in the direction indicted by the arrow 172 while observing the hanging end. Initially the tip 116 of the catheter shaft 112 arced downward (FIG. 13). Once the catheter 110 reached a point such that the exposed portion of the catheter shaft 112 was extended substantially horizontal, as shown in FIG. 14, a measurement was taken (in centimeters) of the length from the edge of the thumb 168 to the tip 116 of the catheter. The length so obtained was reported as the "hand." A larger reading indicates greater catheter stiffness.

Bending Modulus Testing

For purposes of this application, "Bending Modulus" values refer to Bending Modulus values determined using American Society of Testing and Materials (ASTM) Method D747-02 or an equivalent means. The testing used a 0.25 inch span and a weight of 0.06 pounds.

EXAMPLES

Comparative Example 1

Comparative Example 1 was a Bard 16 Fr. 2-way Foley catheter (0165L16) available from C.R. Bard, Inc., Covington, Ga. The catheter had an inner, rubberize layer having a thickness of between about 0.012 inches and about 0.018 inches and formed from a material having a dry Young's Modulus of approximately 36 psi and a wet Young's Modulus of approximately 27 psi, a middle, build up layer having a thickness of between about 0.030 inches and about 0.040 inches and formed from a material having a dry Young's Modulus of approximately 39 psi and a wet Young's Modulus of approximately 27 psi, and an outer, finish layer having a thickness of between about 0.010 inches and about 0.015 inches and formed from a material having a dry Young's Modulus of approximately 39 psi and a wet Young's Modulus of approximately 27 psi. All three layers contained primarily latex rubber and also contained as additives elemental sulfur, zinc oxide, accelerators, and antioxidants (A dithiocarbamate accelerator was used; however, the type of accelerator is not critical or limiting to the invention, and any type of effective accelerator may be used in with latex materials including, but not limited to, other dithiocarbamates, xanthates, thiazoles, thiurams. Similarly although an amine derivative was used as an antioxidant, antioxidants are not critical or limiting to the invention and any type of effective antioxidant may be used including, but not limited to, other amine derivatives as well as phenolic derivatives). The catheter was prepared by successively dipping a form in a composition used to prepare each layer, using the procedures disclosed above. The form had the shape and dimensions of the drainage lumen of the finished catheter such that removal of the mandrel after application and drying of all layers left the drainage lumen in place. The drainage lumen had a diameter of approximately 0.100 inches and the catheter had an outer diameter of 0.208 inches. A reinforcement cap made of woven fabric was also applied over the tip of the catheter after application, but before drying, of the rubberize layer such that the reinforcement cap was located beneath the build up layer. All catheters were coated with a lubricious hydrophilic polyurethane polymer coating.

Example 1

Example 1 Catheters were prepared using the same procedures as those used for the Comparative Example 1 catheters except that the latex material used in the rubberize layer had a dry Young's Modulus of approximately 120 psi and a wet Young's Modulus of approximately 85 psi. The increase in Young's Modulus was accomplished by the addition of MacNamee Clay and Barium Sulfate to the rubberize latex material during formulation. Furthermore, the Example 1 Catheters were prepared without incorporating the reinforcement cap into the catheter tip.

Comparative Example 2

Comparative Example 2 Catheters were prepared using the same procedures as those used for the Comparative Example 1 catheters except that the latex material used in the build up layer had a dry Young's Modulus of approximately 120 psi and a wet Young's Modulus of approximately 85 psi. The increase in Young's Modulus was accomplished by the addition of MacNamee Clay and Barium Sulfate to the rubberize latex material during formulation. Furthermore, the Comparative Example 2 Catheters were prepared without incorporating the reinforcement cap into the catheter tip.

Comparative Example 3

Comparative Example 3 Catheters were prepared using the same procedures as those used for the Comparative Example 1 catheters except that the latex material used in the both the rubberize and the build up layers had dry Young's Modulus of approximately 120 spy and a wet Young's Modulus of approximately 85 psi. The increase in Young's Modulus was accomplished by the addition of MacNamee Clay and Barium Sulfate to the rubberize and build up latex material during formulation. Furthermore, the Comparative Example 3 Catheters were prepared without incorporating the reinforcement cap into the catheter tip.

Samples of the catheters prepared by each Examples 1 and Comparative Examples 1-3 were subjected to "Hand" testing using the procedures provided above. Additional samples of the catheters prepared by each of Example 1 and Comparative Examples 1-3 were subjected to "Tip Penetration" testing using the procedures provided above. Additional samples of the catheters prepared by each of Example 1 and Comparative Example 1 were subjected to "Bending Modulus" testing using the procedures provided above. The Hand measurements, force at penetration from the Tip Penetration Tests, and Bending Modulus measurements are presented in Table 1.

Example 1 as well as Comparative Examples 2 and 3 all had tip penetration values close to those of Comparative Example 1 despite the fact that only Comparative Example 1 included the reinforcement cap.

Only Example 1, having the material with the elevated Young's Modulus in the rubberize layer only, had Hand values similar to that of Comparative Example 1. Comparative Example 2, having elevated Young's Modulus in the build up layer, as well as Comparative Example 3, having elevated Young's Modulus in both the rubberize and build up layers, both had higher hand values, indicating a stiffer catheter. Example 1 also had Bending Modulus values only slightly higher than those of Comparative Example 1.

TABLE 1

Tip Penetration, Hand and Bending Modulus Results.

|  | Tip Penetration (Pounds) | Hand (centimeters) | Bending Modulus (% Load Scale at 50 Degree Angularity) |
| --- | --- | --- | --- |
| Example 1 | 21.77 | 11.31 | 26.8 |
| Comparative Example 1 | 25.73 | 11.27 | 24.4 |
| Comparative Example 2 | 21.38 | 12.83 |  |
| Comparative Example 3 | 19.08 | 13.91 |  |

Comparative Example 4

A chamber was constructed with an opening in one wall through which the shaft of a catheter could be inserted such that part of the catheter is located inside the chamber and part is located outside.

A latex catheter was prepared using identical processes and materials having the same Young's Modulus values as those in COMPARATIVE EXAMPLE 1. The balloon was removed to expose the inflation eye and shaft under the balloon. The catheter was placed through the wall such that the balloon area was located inside the chamber and the opening to the drainage lumen was located outside the chamber. Air pressure was then gradually increased within the chamber. Although the pressure outside the catheter was increased, the internal pressure of the drainage lumen remained at the ambient pressure because the opening of the lumen was outside the chamber. The patency of the inflation lumen was significantly compromised at a chamber pressure of 24 pounds per square inch, gage (psig).

Example 2

COMPARATIVE EXAMPLE 4 was repeated, except that the latex catheter was prepared using materials having the same Young's Modulus values as the materials used in EXAMPLE 1. The patency of the inflation lumen was essentially retained at chamber pressures as high as 40 pounds per square inch, gage (psig).

Example 3

The procedures of COMPARATIVE EXAMPLE 4 are repeated, except that the build up layer, not the rubberize layer, is prepared using materials having the same Young's Modulus values as the materials used on the rubberize layer in EXAMPLE 1. The rubberize layer has the Young's Modulus values of the rubberize layer in COMPARATIVE EXAMPLE 1. The drainage lumen of the resulting catheter does not retain its patency at elevated air pressures as well as the catheters of EXAMPLE 2.

Example 4

A silicone catheter is prepared. The catheter has an inner, rubberize layer made of a silicone material having a wet Young's Modulus of between about 60 psi and about 100 psi, a middle, build up made of a silicone material having a wet Young's Modulus of approximately between about 60 psi and about 100 psi, and an outer, finish layer made of a silicone material having a wet Young's Modulus of approximately between about 60 psi and about 100 psi. The catheter is prepared by co-extruding each layer, followed by drying. The mandrel has the shape and dimensions of the catheter drainage lumen such that removal of the mandrel after fabrication left the drainage lumen in place. The inflation lumen is formed by applying a wire having the desired dimensions of the inflation lumen to the dried rubberize layer before dipping in the build up material. The inflation eye connecting the interior of the balloon with the inflation lumen was cut after application, but before drying, of the build-up level. The application of the finish layer over the build up then provides a balloon that is part of the finish layer.

A second catheter is made that is identical to the first except that the rubberize layer has a wet Young's Modulus of approximately 245 psi. The catheter having the higher Young's Modulus in its rubberize layer retains inflation lumen patency better than that having the lower Young's Modulus.

Example 5

The procedures of EXAMPLE 4 are repeated, but the catheters are made of layers of polyvinyl chlorides. The catheter having the higher Young's Modulus in its rubberize layer retained inflation lumen patency better than that having the lower Young's Modulus in the rubberize layer.

Example 6

The procedures of EXAMPLE 4 are repeated, but the catheters are made of layers of polyurethanes. The catheter having the higher Young's Modulus in its rubberize layer retained inflation lumen patency better than that having the lower Young's Modulus in the rubberize layer.

Example 7

The procedures of EXAMPLE 6 are repeated, but the catheters are made of layers of plastisols. The catheter having the higher Young's Modulus in its rubberize layer retained inflation lumen patency better than that having the lower Young's Modulus in the rubberize layer.

Example 8

The procedures of EXAMPLE 4 are repeated, but the catheters are made of layers of methacrylate. The catheter having the higher Young's Modulus in its rubberize layer retained inflation lumen patency better than that having the lower Young's Modulus in the rubberize layer.

Example 10

The procedures of COMPARATIVE EXAMPLE 1 are repeated, but the catheters are formed using a mandrel with a smaller diameter such that the resulting catheter has a lumen diameter of 0.093 inches. The diameter of the rubberize layer is increased to assure that the catheter retains its outer diameter of approximately 0.020 inches. The catheter shows improved resistance to deflation as compared to the catheter of COMPARATIVE EXAMPLE 1.

Finally, it will be understood that the preferred embodiment has been disclosed by way of example, and that other modifications may occur to those skilled in the art without departing from the scope and spirit of the appended claims.

What is claimed is:

1. A balloon catheter, comprising:
  a catheter shaft including:
    a generally tubular first layer defining a drainage lumen along substantially the entire length of the shaft from a proximal end of the shaft to a distal end thereof, the first layer consisting essentially of a non-metallic material with a first wet Young's Modulus;
    a generally tubular second layer bonded to an outer surface of the first layer, the second layer material having a second wet Young's Modulus less than the first wet Young's Modulus, an inflation lumen extending along the length of the shaft through the second layer from the proximal end of the shaft to a distal portion thereof, the inflation lumen positioned adjacent the first layer outer surface and terminating in an inflation eye extending through an outer surface of the second layer proximate to the distal end of the catheter shaft; and
    a generally tubular third layer, comprising a finish layer, bonded to the second layer outer surface from the proximal end of the shaft to the distal end thereof, the finish layer including a section applied over a pre-formed balloon that is unattached to the second layer outer surface at a circumferential location overlying the inflation eye, the unattached section of the balloon displaceable from the second layer outer surface in response to an inflation medium infused through the inflation eye.

2. The balloon catheter of claim 1, wherein the first wet Young's Modulus is about 1.5 times greater than the second wet Young's Modulus.

3. The balloon catheter of claim 1, wherein the first wet Young's Modulus is about 3 times greater than the second wet Young's Modulus.

4. The balloon catheter of claim 1, wherein the first wet Young's Modulus is greater than or equal to about 50 psi.

5. The balloon catheter of claim 4, wherein the first wet Young's Modulus is greater than or equal to about 80 psi.

6. The balloon catheter of claim 1, wherein the first wet Young's Modulus is in the range of about 70 psi to about 120 psi, and wherein the second wet Young's Modulus is in the range of about 20 psi to about 40 psi.

7. The balloon catheter of claim 1, wherein the first wet Young's Modulus is in the range of about 80 psi to about 90 psi, and wherein the second wet Young's Modulus is in the range of about 20 psi to about 30 psi.

8. The balloon catheter of claim 1, wherein the first wet Young's Modulus is greater than or equal to about 100 psi.

9. The balloon catheter of claim 1, wherein the first wet Young's Modulus is greater than or equal to about 200 psi.

10. The balloon catheter of claim 1, wherein the first wet Young's Modulus is greater than or equal to about 250 psi.

11. The balloon catheter of claim 1, wherein said first layer, said second layer, and said third layer are comprised of silicone.

12. The balloon catheter of claim 1, wherein said first layer, said second layer, and said third layer are comprised of latex.

13. A balloon catheter, comprising:
  a catheter shaft including:
    a tubular first layer defining a drainage lumen along substantially the entire length of the shaft from a proximal end of the shaft to a distal end thereof;
    a tubular second layer bonded to an outer surface of said first layer, the tubular second layer defining an inflation lumen through the second layer along the length of the shaft from the proximal end of the shaft to a distal portion thereof adjacent to said first layer outer surface, the inflation lumen terminating in an inflation eye that extends radially outward through said outer surface of said second layer; and
    a tubular third layer bonded to an outer surface of said second layer from the proximal end of the shaft to the distal end thereof except for a distal portion overlying said inflation eye of said inflation lumen such that a pre-formed balloon and a circumferential portion of said tubular third layer applied over the pre-formed balloon are displaceable away from said underlying portion of said second layer in response to an inflation medium infused through said inflation lumen, through said inflation eye, and into an interstice between said second layer and said third layer;
    wherein a substantially horizontal length of the distal end of the catheter is about 13 centimeters or less in a hand test;
    wherein said catheter lacks any type of tip reinforcement other than said first layer, said second layer, and said third layer; and
    wherein a distal tip of the catheter resists tip penetration of a pin inserted through the drainage lumen when the force applied against the distal tip by the pin is at least about 2.2 pounds.

14. The balloon catheter of claim 13, wherein the distal tip of the catheter resists tip penetration of a pin inserted through the drainage lumen when the force applied against the distal tip by the pin is at least about 10 pounds.

15. The balloon catheter of claim 13, wherein the distal tip of the catheter resists tip penetration of a pin inserted through the drainage lumen when the force applied against the distal tip by the pin is at least about 20 pounds.

16. The balloon catheter of claim 13, wherein a substantially horizontal length of the distal end of the catheter is about 11 centimeters in a hand test.

17. A balloon catheter, comprising:
a catheter shaft including:
a tubular first layer defining a drainage lumen along substantially the entire length of the shaft from a proximal end of the shaft to a distal end thereof;
a tubular second layer bonded to an outer surface of said first layer, the tubular second layer defining an inflation lumen through the second layer along the length of the shaft from the proximal end of the shaft to a distal portion thereof adjacent to said first layer outer surface, the inflation lumen terminating in an inflation eye that extends radially outward through said outer surface of said second layer; and
a tubular third layer bonded to an outer surface of said second layer from the proximal end of the shaft to the distal end thereof except for a distal portion applied over a balloon that is overlying said inflation eye of said inflation lumen such that a portion of the balloon and a circumferential portion of said tubular third layer are displaceable away from said underlying portion of said second layer in response to an inflation medium being infused through said inflation lumen, through said inflation eye, and into an interstice between said second layer and said third layer;
wherein a substantially horizontal length of the distal end of the catheter is about 13 centimeters or less in a hand test; and
wherein the catheter shaft is configured to prevent collapse of the inflation lumen and inflation eye at an inward radial pressure of about 25 psi or less when the drainage lumen is at about atmospheric pressure.

18. The balloon catheter of claim 17, wherein the catheter shaft is configured to prevent collapse of the inflation lumen and inflation eye at an inward radial pressure of up to about 35 psi when the drainage lumen is at about atmospheric pressure.

19. The balloon catheter of claim 17, wherein the catheter shaft is configured to prevent collapse of the inflation lumen and inflation eye at an inward radial pressure of up to about 40 psi when the drainage lumen is at about atmospheric pressure.

20. A balloon catheter, comprising:
a catheter shaft including:
a first layer defining a drainage lumen along substantially the entire length of the shaft from a proximal end of the shaft to a distal end thereof; and
a second layer disposed about the first layer, including an inflation lumen extending along the length of the shaft from the proximal end of the shaft to a distal portion thereof, the inflation lumen terminating in an inflation eye extending radially through an outer surface of the second layer, the first layer comprising a non-metallic material having a first wet Young's Modulus, the second layer comprising a material having a second wet Young's Modulus less than the first wet Young's Modulus;
a third layer bonded to the second layer outer surface from the proximal end of the shaft to the distal end thereof, the third layer including a section applied over a pre-formed balloon that is unattached to the second layer outer surface at a circumferential location overlying the inflation eye, the unattached section of the balloon displaceable from the second layer outer surface in response to an inflation medium infused through the inflation eye.

21. The balloon catheter of claim 20, wherein the first wet Young's Modulus is about 1.5 times greater than the second wet Young's Modulus.

22. The balloon catheter of claim 20, wherein the first wet Young's Modulus is about 3 times greater than the second wet Young's Modulus.

23. The balloon catheter of claim 20, wherein the first wet Young's Modulus is greater than or equal to about 50 psi.

24. The balloon catheter of claim 23, wherein the first wet Young's Modulus is greater than or equal to about 80 psi.

25. The balloon catheter of claim 20, wherein the first wet Young's Modulus is in the range of about 70 psi to about 120 psi, and wherein the second wet Young's Modulus is in the range of about 20 psi to about 40 psi.

26. The balloon catheter of claim 20, wherein the first wet Young's Modulus is in the range of about 80 psi to about 90 psi, and wherein the second wet Young's Modulus is in the range of about 20 psi to about 30 psi.

27. The balloon catheter of claim 20, wherein the first wet Young's Modulus is greater than or equal to about 100 psi.

28. The balloon catheter of claim 20, wherein the first wet Young's Modulus is greater than or equal to about 200 psi.

29. The balloon catheter of claim 20, wherein the first wet Young's Modulus is greater than or equal to about 250 psi.

30. The balloon catheter of claim 20, wherein the first and second layers are comprised of silicone.

31. The balloon catheter of claim 20, wherein the first and second layers are comprised of latex.

32. A balloon catheter, comprising:
a catheter shaft including:
a tubular first layer defining a drainage lumen along substantially the entire length of the shaft from a proximal end of the shaft to a distal end thereof; and
a tubular second layer bonded to an outer surface of said first layer, the tubular second layer defining an inflation lumen through the second layer along the length of the shaft from the proximal end of the shaft to a distal portion thereof adjacent to said first layer outer surface, the inflation lumen terminating in an inflation eye that extends radially outward through said outer surface of said second layer;
a generally tubular third layer, comprising a finish layer, bonded to the second layer outer surface from the proximal end of the shaft to the distal end thereof, the third layer including a section applied over a pre-formed balloon that is unattached to the second layer outer surface at a circumferential location overlying the inflation eye, the unattached section of the balloon displaceable from the second layer outer surface in response to an inflation medium infused through the inflation eye;
wherein a substantially horizontal length of the distal end of the catheter is about 13 centimeters or less in a hand test;
wherein said catheter lacks any type of tip reinforcement other than said first layer, and said second layer, and
wherein a distal tip of the catheter resists tip penetration of a pin inserted through the drainage lumen when the force applied against the distal tip by the pin is at least about 2.2 pounds.

33. The balloon catheter of claim 32, wherein the distal tip of the catheter resists tip penetration of a pin inserted through the drainage lumen when the force applied against the distal tip by the pin is at least about 10 pounds.

34. The balloon catheter of claim 32, wherein the distal tip of the catheter resists tip penetration of a pin inserted through the drainage lumen when the force applied against the distal tip by the pin is at least about 20 pounds.

35. The balloon catheter of claim 32, wherein a substantially horizontal length of the distal end of the catheter is about 11 centimeters in a hand test.

36. A balloon catheter, comprising:

a catheter shaft including:

a generally tubular first layer defining a drainage lumen along substantially the entire length of the shaft from a proximal end of the shaft to a distal end thereof, the first layer consisting essentially of a non-metallic material with a first wet Young's Modulus; and a generally tubular second layer disposed about the first layer, the second layer material having a second wet Young's Modulus less than the first wet Young's Modulus, an inflation lumen extending through the second layer along the length of the shaft from the proximal end of the shaft to a distal portion thereof and terminating in an inflation eye extending radially through the second layer proximate the distal end of the catheter shaft, the catheter shaft configured to prevent collapse of the inflation lumen and inflation eye at inward radial pressures of about 25 psi or less when the drainage lumen is at about atmospheric pressure;

a generally tubular third layer, comprising a finish layer, bonded to the second layer outer surface from the proximal end of the shaft to the distal end thereof, the third layer including a section applied over a preformed balloon that is unattached to the second layer outer surface at a circumferential location overlying the inflation eye, the unattached section of the balloon displaceable from the second layer outer surface in response to an inflation medium infused through the inflation eye.

37. The balloon catheter of claim 36, the catheter shaft configured to prevent collapse of the inflation lumen and inflation eye at inward radial pressures of about 35 psi or less when the drainage lumen is at about atmospheric pressure.

38. The balloon catheter of claim 36, the catheter shaft configured to prevent collapse of the inflation lumen and inflation eye at inward radial pressures of about 40 psi or less when the drainage lumen is at about atmospheric pressure.

39. A catheter, comprising a catheter shaft, a distal catheter tip, and at least one drainage eye proximal of the tip in fluid communication with a drainage lumen extending along substantially the entire length of the shaft from a distal end of the catheter shaft to a proximal end thereof, the catheter shaft including a first layer of latex material having a first wet Young's Modulus of at least about 200 psi, a second layer of latex material having a second wet Young's Modulus less than the first wet Young's Modulus disposed coaxially over the first layer of material, and a third layer of material disposed coaxially over the second layer of material, the second layer including an inflation lumen extending from the proximal end of the shaft to a distal portion thereof and terminating in an inflation eye proximal of the drainage eye, a section of the third layer applied over a balloon that is disposed over the inflation eye displaceable away from the second layer.

40. The balloon catheter according to claim 39, wherein the drainage lumen includes a diameter less than about 50% of an outer diameter of the catheter shaft.

41. The balloon catheter according to claim 39, wherein the drainage lumen includes a diameter in the range of about 40% of an outer diameter of the catheter shaft to about 50% of the catheter shaft outer diameter.

* * * * *